United States Patent
Serhan et al.

(10) Patent No.: US 9,259,730 B2
(45) Date of Patent: Feb. 16, 2016

(54) TUBE TO PRODUCE PLATELET RICH FIBRIN

(71) Applicants: Akman Serhan, Konya (TR); Tunali Mustafa, Ankara (TR)

(72) Inventors: Akman Serhan, Konya (TR); Tunali Mustafa, Ankara (TR)

(*) Notice: Subject to any disclaimer, the term of this patent is extended or adjusted under 35 U.S.C. 154(b) by 0 days.

(21) Appl. No.: 14/350,812

(22) PCT Filed: Oct. 3, 2012

(86) PCT No.: PCT/TR2012/000164
§ 371 (c)(1),
(2) Date: Apr. 10, 2014

(87) PCT Pub. No.: WO2013/062495
PCT Pub. Date: May 2, 2013

(65) Prior Publication Data
US 2014/0241957 A1    Aug. 28, 2014

(30) Foreign Application Priority Data
Oct. 10, 2011    (TR) .................................. 2011/09999

(51) Int. Cl.
*B01L 3/14* (2006.01)
*B01L 3/00* (2006.01)
*B04B 5/04* (2006.01)

(52) U.S. Cl.
CPC .................. *B01L 3/14* (2013.01); *B01L 3/5021* (2013.01); *B01L 2200/0631* (2013.01); *B01L 2200/0647* (2013.01); *B01L 2300/0832* (2013.01); *B01L 2300/0848* (2013.01); *B01L 2400/0409* (2013.01); *B04B 5/0414* (2013.01)

(58) Field of Classification Search
CPC ............ B01L 3/5021; B01L 2200/025; B01L 2300/0858; B04B 5/0414; B04B 2005/0435; B04B 7/08

USPC ................ 422/547–550; 220/315; 494/16, 43
See application file for complete search history.

(56) References Cited

U.S. PATENT DOCUMENTS 5,509,561 A * 4/1996 Kanterovitch ................ 220/4.28
5,552,325 A * 9/1996 Nochumson et al. .......... 436/177

FOREIGN PATENT DOCUMENTS

| EP | 0224927 A2 | 6/1987 |
| EP | 2360470 A1 * | 8/2011 |
| GB | 2033257 A | 5/1980 |
| WO | WO 9912661 A1 | 3/1999 |
| WO | WO2010020247 A1 | 2/2010 |

OTHER PUBLICATIONS

Dohan et al:"Platelet-rich fibrin(PRF): A second-generation platelet concentrate. Part I: Technological concepts and evolution". Oral Surgery, Oral Medicine, Oral Pathology.
Harish Saluja et al: Platelet-Rich fibrin: A second generation platelet concentrate and a new friend of oral and maxillofacial surgeons, Anmals of Maxillofacial Surgery.

* cited by examiner

*Primary Examiner* — Dennis M White
*Assistant Examiner* — Bryan Kilpatrick
(74) *Attorney, Agent, or Firm* — Gokalp Bayramoglu

(57) ABSTRACT

Invention; It is about the tubes used to obtain blood products through centrifuge in order to cure open and closed injuries, to heal hard and soft tissues and to diagnose in all fields of medicine and dentistry. Platelet Rich Fibrin (PRF) obtained in the tubes the surface of which contacts blood and made from pure titanium or titanium alloys has a better structure of fibrin than that is obtained through classical methods. The efficiency of the high speed centrifuge is increased with this designed tube and Platelet Rich Fibrin can be removed from the tube without spoiling it.

Figure 1:
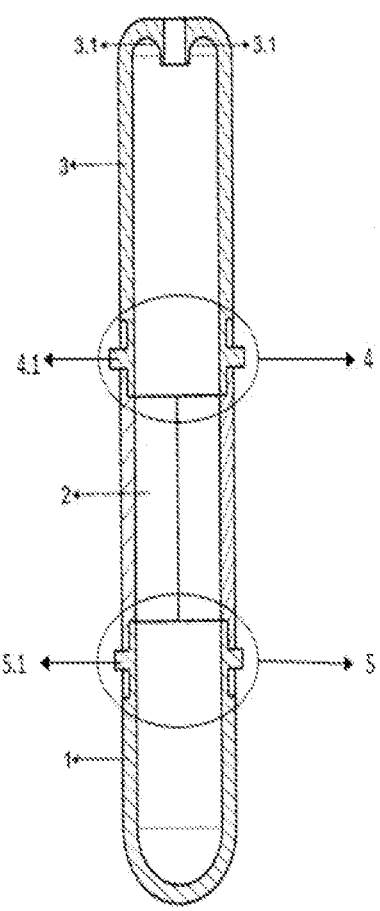

11 Claims, 2 Drawing Sheets

TUBE TO PRODUCE PLATELET RICH FIBRIN

TECHNICAL FIELD

Invention; It is about the tubes used to obtain blood products through, centrifuge in order to cure open and closed injuries, to heal hard and soft tissues and to diagnose in all fields of medicine and dentistry.

PRIOR ART

The use of fibrin adhesives in stimulating wound healing and blood by-products in wound closures started 40 years ago. Fibrin is the activated state of plasmatic molecule fibrinogen. These soluble fibrils exist in high quantities in the α-granules of the thrombocytes and molecule plasma and act an important role in thrombocyte aggression during hemostasis.

In fact, fibrogen is the last product of all coagulation reactions. Fibrinogen, the soluble protein, turns into nonsoluble structure fibrin through thrombin. It forms the first cicatricial matrix of the damaged area in the polymerized gel. This structure which turns into biological adhesive builds a protective wall for the vascular structure around the first developed thrombocyte heaps during coagulation.

Thrombocytes are the cells that have essential role in coagulation and prevent excessive blood loss during blood vessel injuries. Thrombocytes include a great many cytokine and growing factors causing bone degeneration and soft tissue maturation. The key growth factors Platelet Derived Growth Factor AB (PDGF-AB), Transforming Growth Factor β-1 (TGFβ-1), Vascular Endothelial Growth Factors (VEGF) exist densely in thrombocytes. These growth factors have the potency of stimulating cell multiplication, matrix remodeling and angiogenesis. In the last 20 years, it has been suggested that this cell can be used as a cure because it has been found out better that thrombocytes have an important role in healing wounds.

Platelet Rich Plasma (PRP)

Autogenous preparation called Platelet Rich Plasma (PRP) has been used widely in orthopedy, plastic surgery and dentistry. While there are some studies on Platelet Rich Plasma (PRP) with different results, it is a predominant view that it affects the wound healing positively.

One of the important factors determining the features of the Platelet Rich Plasma (PRP) preparation is the substances that will be added to the preparation and provide coagulation. The alterations in the amount and quantity of the substances added have brought about developing a great number of Platelet Rich Plasma (PRP) methods. Platelet Rich Plasma (PRP) methods still keep their actuality today.

Platelet Rich Fibrin (PRF)

Platelet Rich Fibrin (PRF), in other words thrombocyte rich fibrin, is the second generation thrombocyte concentration developed after Platelet Rich Plasma (PRP) by Dr. Joseph Choukroun in 2001 in France. Platelet Rich Fibrin (PRF) has been described as a leucocyte and thrombocyte rich autologous fibrin biomaterial. Unlike other platelet rich products, this technique does not require anticoagulant, bovine thrombin, calcium chloride or any gelling agents. In this technique, blood is filled into the glazed plastic or glass tubes at once and centrifuged at proper speed. Three layers occur in the tube at the end of centrifuge.

The layer of the red blood cells accumulated at the bottom of the tube

Acellular plasma with low thrombocytes accumulates at the top of the tube

Platelet Rich Fibrin that is PRF coagulum comes off in the middle of the tube.

After the centrifuge procedure, leucocyte and platelet rich coagulum created through natural coagulation mechanism can be obtained without having to do any biochemical modification of blood.

PRF Protocol:

The protocol used for PRF practices nowadays:

Venous blood (~10 ml) obtained from the case is placed at once into a silicon tube the inside of which is glazed or a glass tube containing no anticoagulant.

Since the platelet activation and fibrin polymerization are triggered immediately in the lack of anticoagulant, the tube is centrifuged at once in the centrifuge previously adjusted to 2700 RPM for 12 min or 3000 RPM for 10 min.

Following the centrifuge procedure, a layer of the red blood cells accumulated at the bottom of the tube, acellular plasma with low thrombocytes at the top of the tube and Platelet Rich Fibrin, that is PRF coagulum comes off in the middle of the tube, Platelet Rich Fibrin (PRF) creates a complex three dimensional fibrin matrix. Majority of the platelet and leucocytes of the obtained blood accumulate in this fibrin matrix. The emanated coagulum is removed with a dental tweezers and used as it is, or Platelet Rich Fibrin (PRF) coagulum can be turned into membrane by compressing.

The fields where Platelet Rich Fibrin (PRF) and Platelet Rich Fibrin (PRF) membrane are used in medicine and dentistry: in reinforcing the healing of soft tissues, in the practices of tissue regeneration guided by bone grafting and guided bone regeneration, and covering sinus membrane perforations. Furthermore, it can be used to restore acquired or created bone defects and Platelet Rich Fibrin (PRF) dental implant can also be used for the primary or secondary bone losses that may occur around dental implants.

The problems caused by using glazed or glass tubes to obtain Platelet Rich Fibrin (PRF): It has been claimed that;

Glass and glazed silicon tubes affect the formation of fibrin structure,

Silica particles in the glass have harmful effects. Moreover, even if the blood in the tubes is centrifuged at higher speeds, it should not contact the materials such as the tube caps not made of proper materials that may impair the fibrin structure.

BRIEF ABSTRACT OF THE INVENTION

Platelet Rich Fibrin (PRF) obtained in the tubes the surface of which contacts blood and made from pure titanium or titanium alloys has a better structure of fibrin than that is obtained through classical methods. The efficiency of the high speed centrifuge is increased with this designed tube and Platelet Rich Fibrin can be removed from the tube without spoiling it.

LIST OF FIGURES

Figure 2:
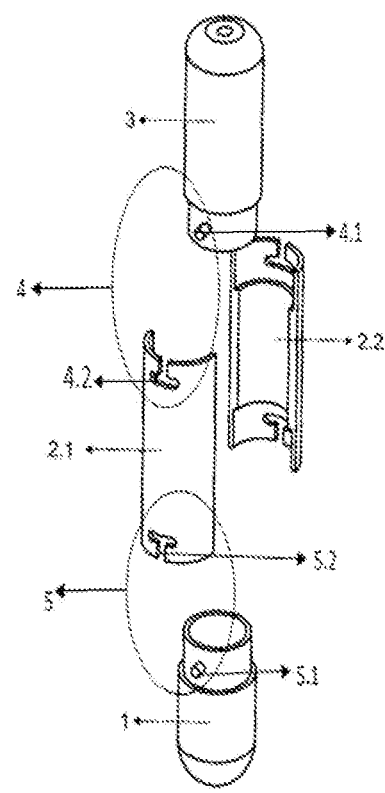

FIG. 1. Sectional view
FIG. 2. Exploded view

DESCRIPTION OF THE REFERENCE NUMERALS

1 Lower body
2 Trunk
2.1 Right part
2.2 Left part

3 Upper body
3.1 Concave curve
4 Upper lock mechanism
4.1 fixed key
4.2 groove
5 Lower lock mechanism
5.1 fixed key
5.2 groove

DETAILED DESCRIPTION OF THE INVENTION

The invention consists of the parts of the lower body (1), trunk (2), made up of the combination of the right part (2.1) and left part (2.2), and upper body (3) including concave curve (3.1) at the top.

The concave curve (3.1) at the top of the upper body (3) of the tube enables the elevated blood to descend again during the high speed centrifuge. The concave curve (3.1) has been shaped concordant with the cylindrical structure of the tube. Furthermore, thanks to the concave curve (3.1), the tube does not require a cap. This state prevents any negative results that may be caused by the contact of blood with the cap during the high speed centrifuge. Moreover, generally in all high speed centrifuges, the concave curve (3.1) designed in our invention will enhance the efficiency of the centrifuge making the elevated liquid during centrifuge descend again.

The lock system includes two upper lock mechanisms (4) located between the upper body (3) and the trunk (2) and two lower lock mechanisms (5) located between the lower body (1) and the trunk (2). Each of the lock mechanisms include a fixed key and a "T" shape groove. Especially, a first upper lock mechanism (4) includes a fixed key (4.1) located on the outer surface of the upper body (3) adjacent to the right part (2.1), and a "T" shape groove (4.2) on the top of the right part (2.1); a second upper lock mechanism (4) includes a fixed key (4.1) located on the outer surface of the upper body (3) adjacent to the left part (2.2), and a "T" shape groove (4.2) on the top of the left part (2.2). Groove (4.2) matches with fixed key (4.1) to lock trunk (2) and upper body (3). The two upper lock mechanisms (4) are symmetrically disposed on the tube. A first lower lock mechanism (5) has a fixed key (5.1) located on the outer surface of lower body (1) adjacent to the right part (2.1), and a "T" shape groove (5.2) located on the bottom of the right part (2.1); a second lower lock mechanism (5) has a fixed key (5.1) located on the outer surface of lower body (I) adjacent to the left part (2.2), and a "T" shape groove (5.2) located on the bottom of the left part (2.2). Groove (5.2) matches with fixed key (5.1) to lock trunk (2) and lower body (l). The two lower lock mechanisms (5) are symmetrically disposed on the tube. An external diameter of the bottom part of upper body (3) is substantially equal to an internal diameter of the top part of the trunk (2). Thus, upper body (3) can match with trunk (2). An external diameter of the top part of lower body (1) is substantially equal to an internal diameter of the bottom part of the trunk (2). Thus, lower body (1) can match with the trunk (2).

Platelet Rich Fibrin (PRF) can be removed without being spoilt when the right part (2.1) and left part (2.2) constituting trunk (2) disconnect after centrifuge. The diameter and thickness of Platelet Rich Fibrin that will come off in centrifuge; can be adjusted by modifying the amount of blood put in the tube, and the diameter of the trunk (2) where Platelet Rich Fibrin occurs.

Titanium is resistant to corrosion and a biocompatible material and has the property of osteointegration. Because of this feature, it has been used in dental implants as well. It is a favorable material to produce Platelet Rich Fibrin and other blood products.

The tubes the surface of which contacts blood and made from pure titanium or titanium alloy are more successful at platelet aggregation than glazed silicon and glass tubes.

Enlarging the interior surface of the tube that contacts blood has positive results in order to obtain Platelet Rich Fibrin in a short time. Enlarging the surface of the tube the surface of which contacts blood and made up of pure titanium or titanium alloy is achieved through sandblasting, laser and similar ways. Thus, by enlarging the contact surface of the blood with pure titanium, the quality and speed of obtaining Platelet Rich Fibrin increase.

Within our invention, blood is placed into the tube at once in order to produce Platelet Rich Fibrin. It is centrifuged at proper rotation and duration. Three layers occur at the end of the centrifuge The layer of red blood cells accumulated in the lower body (1), Platelet Rich Fibrin (PRF) formed in the trunk (2) of the tube, Acellular plasma lack of platelet accumulated in the upper body (3).

Following the centrifuge procedure, Platelet Rich Fibrin (PRF) is obtained without exposing the blood to any biochemical modification. Our invention can contribute to develop Platelet Rich Fibrin (PRF) that has been used in many studies and its clinical significance is gradually increasing. The difference between the Platelet Rich Fibrin (PRF) obtained centrifuging with our invention and the Platelet Rich Fibrin (PRF) obtained centrifuging with glass and glazed silicon tubes; ours is more homogeneous and has a better fibrin plexus. Platelet Rich Fibrin (PRF) can be used in a large number of in-vitro and in-vivo studies.

The invention claimed is:
1. A tube for producing platelet rich fibrin, comprising:
a lower body which is able to isolate the blood products formed following the centrifuge procedure;
a trunk made up of a left part, a right part;
an upper body having a concave curve shape at top center;
wherein the left part and the right part are respectively locked with the upper body and lower body by a lock system;
wherein the lower body, the left part, the right part and the upper body are dismantled; and wherein the inner surfaces of the upper body, the trunk, and the lower body are coated with pure titanium that increases the contact surface of blood during centrifuge and has increased surface area.

2. The tube according to claim 1, wherein the fibrin is collected by removing the left part and the right part of the trunk after centrifuge process.

3. The tube according to claim 1, wherein the thickness and the diameter of platelet rich fibrin is adjustable by modifying the amount of blood placed in the tube, and by adjusting the inner geometry of the trunk.

4. A tube for producing platelet rich fibrin, wherein the inner surfaces of the tube which contact blood during centrifuge are made up of pure titanium or titanium alloy, and wherein the inner surfaces of the tube which contact blood are increased; comprising:
a lower body which is able to isolate the blood products formed following the centrifuge procedure;
a trunk made up of a left part, a right part;
an upper body;
wherein the left part and the right part are respectively locked with the upper body and lower body by a lock system; and
wherein the lower body, the left part, the right part and the upper body are dismantled.

5. The tube according to claim 4, wherein the upper body has a concave curve shape that increases the homogenization of the blood products and centrifuge efficiency.

6. The tube according to claim 4, wherein the fibrin is collected by removing the left part and the right part of the trunk after centrifuge process.

7. The tube according to claim 4, wherein the thickness and the diameter of platelet rich fibrin is adjustable by modifying the amount of blood placed in the tube, and by adjusting the inner geometry of the trunk.

8. The tube according to claim 1, wherein the lock system includes at least two lock mechanism, and wherein the lock mechanism includes a fixed key and a "T" shape groove.

9. The tube according to claim 8, wherein the fixed key is located on the outer surface of the lower body adjacent to the right part, and the "T" shape groove located on the bottom of right part.

10. The tube according to claim 4, wherein the lock system includes at least two lock mechanism, and wherein the lock mechanism includes a fixed key and a "T" shape groove.

11. The tube according to claim 10, wherein the fixed key is located on the outer surface of the lower body adjacent to the right part, and the "T" shape groove located on the bottom of right part.

* * * * *